United States Patent [19]

Sager

[11] Patent Number: 4,747,619

[45] Date of Patent: May 31, 1988

[54] PRESSURE-SENSITIVE LABEL

[75] Inventor: Frank D. Sager, Centerville, Ohio

[73] Assignee: NCR Corporation, Dayton, Ohio

[21] Appl. No.: 34,375

[22] Filed: Apr. 6, 1987

[51] Int. Cl.[4] ........................ B41L 1/20; B42D 15/00; B32B 31/00; A61F 13/02

[52] U.S. Cl. ...................................... 282/9 R; 283/81; 156/249; 428/40

[58] Field of Search .................. 283/81; 156/231, 235, 156/238, 239, 241, 249; 428/40, 41, 42, 77, 78; 40/2 R; 282/9 R

[56] References Cited

U.S. PATENT DOCUMENTS

| | | | |
|---|---|---|---|
| Re. 32,249 | 9/1986 | Esmay . | |
| 4,358,494 | 11/1982 | Akimato et al. . | |
| 4,495,016 | 1/1985 | Viberg et al. | 428/40 |
| 4,513,039 | 4/1985 | Esmay | 428/40 |
| 4,521,267 | 6/1985 | Jacobson | 428/40 |
| 4,526,405 | 7/1985 | Hattemer | 428/40 |
| 4,528,055 | 7/1985 | Hattemer | 428/40 |
| 4,554,193 | 11/1985 | Erickson | 428/40 |
| 4,557,971 | 12/1985 | Williams . | |
| 4,582,736 | 4/1986 | Duncan . | |
| 4,598,003 | 7/1986 | Renholts . | |
| 4,604,153 | 8/1986 | Melbye | 428/40 |
| 4,614,361 | 9/1986 | Foster . | |
| 4,619,858 | 10/1986 | Dam et al. . | |
| 4,636,432 | 1/1987 | Shibano et al. . | |

*Primary Examiner*—E. R. Kazenske
*Assistant Examiner*—Paul M. Heyrana, Sr.
*Attorney, Agent, or Firm*—Wilbert Hawk, Jr.; Albert L. Sessler, Jr.; George J. Muckenthaler

[57] ABSTRACT

A multiple-layered medium includes a preprinted image and impact imaged variable information applied to a surface. Subsequently, a layered portion containing such image and information is separated from the remaining layered portion which also retains such image and information. The multiple layered medium provides a pressure-sensitive label that is fastened by adhesive to a surface and a non-adhesive portion of the label that is separated from the fastened portion.

10 Claims, 1 Drawing Sheet

PRESSURE-SENSITIVE LABEL

BACKGROUND OF THE INVENTION

In the field of labels or like media of the pressure-sensitive type, conventional manufacture involves the use of a pressure-sensitive material applied to a substrate or face stock, usually paper, in the form of a continuous web and then dried. A release sheet or liner, usually provided as a continuous paper web that is coated with a release agent, is applied to the exposed pressure-sensitive material adhesive surface to form a substrate-pressure-sensitive adhesive-release sheet label stock.

Representative documentation in the field of pressure-sensitive labels or the like includes U.S. Pat. No. 4,358,494, issued to S. Akimato et al. on Nov. 9, 1982, which discloses a process for preparation of paper backed adhesive tapes of the pressure-sensitive type. The tape includes film, paper, a polyethylene coat for the release layer, and a pressure-sensitive adhesive.

U.S. Pat. No. 4,557,971, issued to R. Williams on Dec. 10, 1985, discloses a multiple layered markable and self-adhereable tape that includes a permeable layer, an upper strength film layer, a weak carrier layer of paper, and water soluble adhesive. The tape may be stuck to itself.

U.S. Pat. No. 4,582,736, issued to G. L. Duncan on Apr. 15, 1986, discloses coextended pressure-sensitive label stock material with integral peelable backing.

U.S. Pat. No. 4,598,003, issued to R. J. Renholts on July 1, 1986, discloses an imprintable tape that has an opaque film portion formed from polytetrafluoroethylene (PTFE) and a layer of material of contrasting color wherein impact causes the PTFE to become transparent and to form a contrasting indicia or design. Also, the tape has an adhesive layer covered by a removable backing, and it may also have a protective film.

U.S. Pat. No. Re. 32,249, issued to D. L. Esmay on Sept. 23, 1986, (Reissue of U.S. Pat. No. 4,522,870), discloses a linerless double-coated pressure-sensitive adhesive tape wherein the adhesive at each face is a solvent free, crosslinked alkyl acrylate polymer to permit winding upon itself.

U.S. Pat. No. 4,614,361, issued to R. S. Foster on Sept. 30, 1986, discloses a multiple part shipping label having an upper layer of stencil paper, a removable lower layer with an adhesive coating and an intermediate layer.

U.S. Pat. No. 4,619,858, issued to E. Dam et al. on Oct. 28, 1986, discloses adhesive paper material and a label made from such material that includes a thin paper web and a thin plastic sheet of polyester or similar material.

And, U.S. Pat. No. 4,636,432, issued to T. Shibano et al. on Jan. 13, 1987, discloses a pressure-sensitive adhesive tape having a substrate, a release layer and a mass layer, the tape having an adhesion of no more than 150 g/cm.

SUMMARY OF THE INVENTION

The present invention relates to pressure-sensitive labels that can be imprinted with variable information and then applied to a surface. The variable information is that information which is printed on a labeled surface and on a portion separable therefrom. In addition to the variable information, a preprinted image can be applied to the surface. The label is named a dry tag label by reason that a portion of the label can be removed from the surface for use as an invoice or to transfer the variable information to another location. An example of the use of a pressure sensitive label according to the structure of the present invention is for letter or package application wherein the information on the labeled surface stays with the letter or package as a permanent record and the dry portion is removed for use as a separate record.

The portion of the label, in the form of a dry tag or card that is removed or separated from the surface, includes all or a part of the printing thereon. In other words, the preprinted image that remains on the surface may or may not be the same image as the preprinted image on the dry tag or card. However, the variable information that was printed prior to separation or removal of the portion remains on both the dry tag or card and on the labeled surface.

The label essentially consists of a plurality of layers of material that are formed or constructed in a laminated arrangement. A first material portion includes a face stock, a pressure-sensitive adhesive and a release liner. A second material portion includes a first transparent plastic film, a "fugitive" or non-tacky adhesive, a second transparent plastic film, a pressure-sensitive adhesive, and a release liner. The "fugitive" adhesive is a term in the art which indicates an adhering quality or characteristic when in contact with other media but which does not have such adhering quality or characteristic when separated from the media. A third material portion includes a self contained carbonless paper face stock, a pressure-sensitive adhesive and a release liner.

The dry tag label, before application onto a surface, includes the three material portions in a laminated arrangement; however, with the release liner only on the third material portion. When the dry tag label is applied onto a surface, the release liner is removed from the third material portion so that the pressure-sensitive adhesive is effective to fasten the label onto the surface. The dry tag or card is then removed or separated along the plane of the fugitive or non-tacky adhesive from the permanent portion of the label for use at another location.

In accordance with the above discussion, a principal object of the present invention is to provide a pressure-sensitive label formed of several material portions.

Another object of the present invention is to provide a pressure-sensitive label of multiple layers of face stock and film along with pressure-sensitive adhesive and non-tacky adhesive.

An additional object of the present invention is to provide a pressure-sensitive label wherein a preprinted image and impact imaged variable information can be applied onto a surface and then separated from a label portion fixed to the surface.

A further object of the present invention is to provide a pressure-sensitive label that is formed of multiple layers and includes a plurality of material portions in laminated manner and wherein a portion of the label can be separated from a permanent label portion for use at another location.

Additional advantages and features of the present invention will become apparent and fully understood from a reading of the following description taken together with the annexed drawing.

DESCRIPTION OF THE PREFERRED EMBODIMENT

Figure 1:
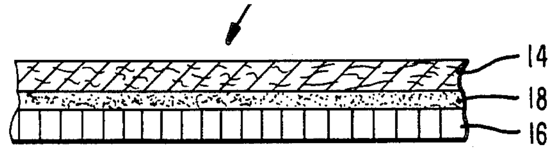
FIG. 1 is a sectional view of a first material portion of the label.

Referring now to the drawing, the pressure-sensitive label is designed to carry a preprinted image and impact imaged variable information which image and information can be applied to a surface. After application of such image and information onto the surface, a portion of the label, designated as a non-adhesive dry tag portion or card having the image and information thereon, can be separated from the remainder of the label that is permanently attached or fixed to the surface, and then moved to another location.

The pressure-sensitive label of the present invention is constructed from separate material portions or products. FIG. 1 illustrates a first material portion 12 of a label that includes a face stock layer 14 of paper or like fiber material and a release liner or layer 16 of densified paper or like material that are adhered in laminated manner by the use of a layer of pressure-sensitive adhesive 18. The portion 12 constitutes a pressure-sensitive material laminate.

Figure 2:
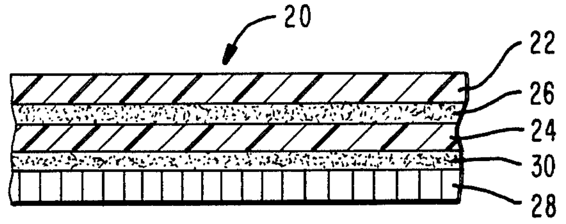
FIG. 2 is a sectional view of a second material portion of the label.

FIG. 2 illustrates a second material portion 20 of the label that includes a transparent plastic film 22 and a transparent plastic film 24 of olefin or like material with a layer of fugitive or non-tacky adhesive 26 between the films. A release liner or layer 28 is adhered to the film 24 in laminated manner by the use of a layer of pressure-sensitive adhesive 30. The portion 20 constitutes a pressure-sensitive material called Coupon Base.

Figure 3:
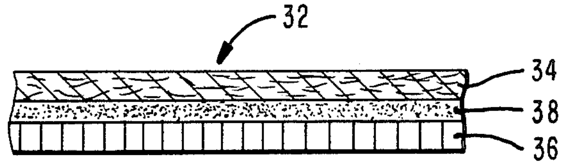
FIG. 3 is a sectional view of a third material portion of the label.

FIG. 3 illustrates a third material portion 32 of the label that includes a self-contained carbonless paper face stock layer 34 and a release liner or layer 36 that are adhered in laminated manner by the use of a layer of pressure-sensitive adhesive 38. The portion 32 constitutes a special pressure-sensitive material laminate by reason of the self contained carbonless paper utilized therein.

In the preparation of the pressure-sensitive label, indicated as 40, (FIG. 4) preprinting of a desired image is accomplished on the top surfaces of portions 12, 20 and 32 prior to laminating the several layers of each portion. The preprinting on the top surface of portion 20 will appear as back printing on the dry tag label portion of the label. The preprinting on the top surface of portion 32 will be protected by the plastic film layer 22 of the second material portion 20.

Figure 4:
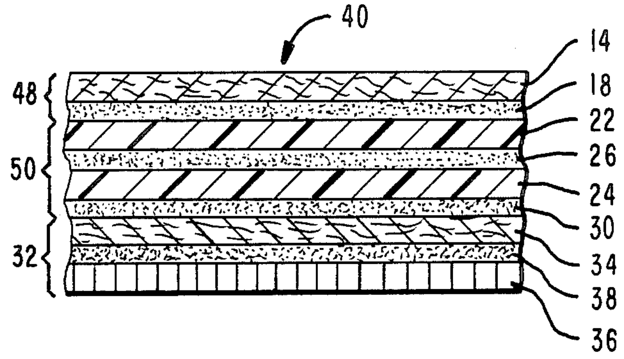
FIG. 4 is a sectional view of the label prior to application onto a surface.

The assembly of the pressure-sensitive label 40, illustrated in FIG. 4, is accomplished by first removing and discarding the release liner 16 from material portion 12. The remainder of the material portion 12, now consisting of the layers 14 and 18, and indicated as portion 48 rn FIG. 4, is laminated to the plastic film 22 of the material portion 20 by means of the adhesive layer 18 of such remainder portion 48 of material portion 12.

Next, the release liner 28 is removed and discarded from the material portion 20 to provide a remainder portion, indicated as portion 50 in FIG. 4, and the portions 48 and 50 are laminated to the top layer 34 of portion 32 by means of the adhesive layer 30 to form the pressure-sensitive label shown in FIG. 4.

Additional information is then printed on the pressure-sensitive label 40 by any suitable impact printing device. Of course, hand written information can be applied with firm pressure to form a legible image on the self-contained carbonless face stock layer 34.

Figure 5:
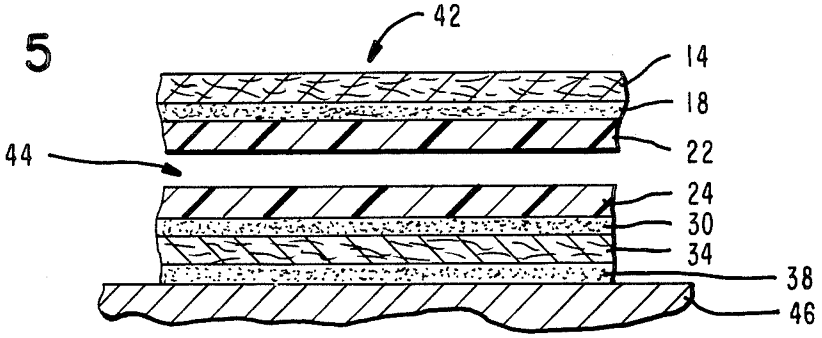
FIG. 5 is a sectional view of the applied label and showing the dry tag portion separated from the permanent portion.

FIG. 5 illustrates the use of the pressure-sensitive label 40 (FIG. 4) wherein the release liner 36 is removed therefrom and the label is applied to a surface 46. The adhesive 38 causes the label 40 to adhere to the surface 46. The label portion 42, a dry tag or non-adhesive portion of the label 40, is removed from the remaining portion 44 by separating the portions by means of relieving of the fugitive or non-tacky adhesive between the plastic films 22 and 24. The portion 42, consisting of layers or plies 14, 18 and 22 is used as a tag or a card at another location. The portion 44, consisting of layers or plies 24, 30, 34 and 38, remains on the labeled surface 46.

In a selection of materials used in the present invention, the preferred face stock 14 is paper or like fibrous material, and the transparent plastic films 22 and 24 are olefin or like synthetic plastic film material. The second material portion 20 consists of several layers called "Coupon Base" and is available from Fasson, Roll Materials Division, Painesville, Ohio, 44077. Fasson is a registered trademark of Avery International Corporation. The pressure-sensitive adhesive 18, 30 and 38 is a rubber-based permanent type and the non-tacky adhesive 26 is a proprietary adhesive, designated as S-246, and available from Fasson. The self-contained carbonless paper face stock 34 is coated on its front surface and the release lineres layers 16, 28 and 38 are densified Kraft paper.

It is thus seen that herein shown and described is a pressure-sensitive label that includes a plurality of layers of different materials that provide for a dry tag removable portion and a permanent label portion to provide at least two independent records of the information. The present invention enables the accomplishment of the objects and advantages mentioned above, and while a preferred embodiment of the invention has been disclosed herein, variations thereof may occur to those skilled in the art. It is contemplated that all such variations and modifications not departing from the spirit and scope of the invention hereof are to be construed in accordance with the following claims.

I claim:

1. A pressure-sensitive label suitable for imprinting images thereon comprising a plurality of layers of record media, at least one of the layers being fiber stock and a pair of other layers being synthetic stock, said at least one layer of fiber stock and at least one of the pair of other layers of synthetic stock having preprinted images on one surface thereof, the preprinted images on said one surface being protected by the other one of the pair of layers of synthetic stock; a layer of pressure-sensitive adhesive for causing adherence of said at least one fiber stock layer with one of the pair of synthetic stock layers; a layer of non-tacky adhesive positioned in contact with the synthetic stock layers for allowing separation of one synthetic stock layer from the other synthetic stock layer; and a carbonless fiber layer adhered to the other of said synthetic stock layers for receiving impringting images on said carbonless fiber layer after laminating the layer of fiber stock, the layers of synthetic stock and the carbonless fiber layer, and a layer of pressure-sensitive adhesive for securing said carbonless fiber layer to a fixed surface, the separation of said one synthetic layer from the other synthetic layer providing a non-adhesive label portion removable from said other synthetic stock layer and the carbonless fiber layer.

2. The pressure-sensitive label of claim 1 wherein the fiber stock is paper and wherein the synthetic stock is plastic.

3. The pressure-sensitive label of claim 1 wherein the carbonless fiber layer comprises a self-contained carbonless layer.

4. A method of making a pressure-sensitive label for receiving imprinted images thereon comprising the steps of:

providing at least one layer of fiber stock and a plurality of layers of synthetic stock;

printing images on one surface of the fiber stock, adhering said at least one fiber stock layer with at least one of the synthetic stock layers;

releasably adhering the layers of synthetic stock with non-tacky adhesive to allow separation thereof;

printing images on one surface of said one layer of synthetic stock, the other of said layers of synthetic stock protecting the images on said one layer of synthetic stock, adhering a carbonless fiber layer with the other of said synthetic stock layers;

printing images on one surface of said carbonless fiber layer after laminating the fiber stock and the layers of synthetic stock, adhering a portion of the pressure-sensitive label to a surface, and removing a non-adhesive portion of the pressure-sensitive label for use at another location.

5. The method of claim 4 wherein the fiber stock is paper and the synthetic stock is plastic.

6. The method of claim 4 wherein the carbonless fiber layer comprises a self-contained carbonless layer.

7. A pressure-sensitive label for receiving imprinted images comprising a first material portion having a fiber stock layer and a release layer, means adhereing the fiber stock layer and the release layer of the first material portion, a second material portion having a pair of synthetic stock layers comprising a first synthetic stock layer and a second synthetic stock layer and a release layer, means adhereing the second mentioned release layer and said first one of said synthetic stock layers, and a layer of non-tacky adhesive in contact with said pair of synthetic stock layers for enabling separation thereof, and a third material portion having a carbonless fiber stock layer and a release layer adhered thereto, the top surfaces of each of said first, second, and third material portions enabling printing of images thereon, the release layer of the first material portion and the release layer of the second material portion being capable of being removed from said first and second portions, and said first material portion and said second material portion being laminated with said third material portion to form a label assembly, the label assembly enabling additional printing of images on the carbonless fiber stock layer thereof, the fiber stock layer of the first material portion and said second one of the synthetic stock layers of the second material portion being removed from the first one of the synthetic stock layers and the carbonless fiber stock layer to provide a non-adhesive portion of the pressure-sensitive label for use at another location.

8. The pressure-sensitive label of claim 7 wherein the fiber stock comprises paper and the synthetic stock comprises plastic.

9. The pressure-sensitive label of claim 7 wherein the fiber stock layer of said third material portion comprises self-contained carbonless paper.

10. The pressure-sensitive label of claim 7 wherein the first material portion less the release liner and one of said synthetic stock layers of said second portion are removable as a unit from the remainder of the second material portion less the release liner and from the third material portion to form a dry label.

* * * * *

UNITED STATES PATENT AND TRADEMARK OFFICE

CERTIFICATE OF CORRECTION

PATENT NO. : 4,747,619

DATED : May 31, 1988

INVENTOR(S) : Frank D. Sager

It is certified that error appears in the above—identified patent and that said Letters Patent is hereby corrected as shown below:

Column 5, line 4, delete "impringting" and substitute --imprinting--.

Column 6, line 5, delete "adhereing" and substitute --adhering--.

Column 6, line 11, delete "adhereing" and substitute --adhering--.

Column 6, line 31, delete "removed" and substitute --removable--.

Signed and Sealed this

Eighteenth Day of October, 1988

*Attest:*

DONALD J. QUIGG

*Attesting Officer*

*Commissioner of Patents and Trademarks*